(12) United States Patent
Tager

(10) Patent No.: US 7,299,568 B2
(45) Date of Patent: Nov. 27, 2007

(54) ORTHOPEDIC FOOT DEVICES

(76) Inventor: Steven E. Tager, 303 Pasadera Ct., Monterey, CA (US) 93940

( * ) Notice: Subject to any disclaimer, the term of this patent is extended or adjusted under 35 U.S.C. 154(b) by 13 days.

(21) Appl. No.: 10/940,651

(22) Filed: Sep. 15, 2004

(65) Prior Publication Data

US 2006/0053664 A1    Mar. 16, 2006

(51) Int. Cl.
    *A61F 5/14*      (2006.01)
(52) U.S. Cl. .......................... 36/140; 36/144
(58) Field of Classification Search ............ 36/38, 36/140, 143, 144, 180, 181
See application file for complete search history.

(56) References Cited

U.S. PATENT DOCUMENTS

| | | | |
|---|---|---|---|
| 1,656,556 A | 1/1928 | Brown | |
| 2,089,384 A | 8/1937 | Levitt | |
| 2,310,824 A | 2/1943 | Wyant | |
| 2,567,028 A | 9/1951 | Rapisarda | |
| 2,616,190 A | 11/1952 | Darby | |
| 2,979,835 A * | 4/1961 | Scholl | 36/44 |
| 2,990,629 A | 7/1961 | McLaughlin | |
| 3,605,294 A | 9/1971 | Cunningham et al. | |
| 3,984,926 A | 10/1976 | Calderon | |
| 4,333,472 A * | 6/1982 | Tager | 36/140 |
| 4,442,612 A | 4/1984 | Hauser | |
| 4,513,518 A | 4/1985 | Jalbert et al. | |
| 4,517,981 A | 5/1985 | Santopietro et al. | |
| 4,572,196 A | 2/1986 | Prahl | |
| 4,578,882 A | 4/1986 | Talarico, II | |
| 4,620,376 A | 11/1986 | Talarico, II | |
| 4,627,177 A | 12/1986 | Meyers | |
| 4,642,911 A | 2/1987 | Talarico, II | |
| 4,642,912 A * | 2/1987 | Wildman et al. | 36/44 |
| D291,742 S | 9/1987 | Surpuriya et al. | |
| 4,747,410 A | 5/1988 | Cohen | |
| 4,793,078 A | 12/1988 | Andrews | |
| 4,803,989 A | 2/1989 | Collins | |
| 4,813,157 A | 3/1989 | Boisvert et al. | |
| 4,862,605 A | 9/1989 | Gardner et al. | |
| 4,882,856 A | 11/1989 | Glancy | |

(Continued)

FOREIGN PATENT DOCUMENTS

WO    WO 91/07152    5/1991

(Continued)

OTHER PUBLICATIONS

International Search Report, International Application No. PCT/US2005/032580 (Jan. 26, 2006).

*Primary Examiner*—Ted Kavanaugh
(74) *Attorney, Agent, or Firm*—Arnold & Porter LLP

(57) ABSTRACT

An orthopedic device for correction of varus, valgus, or supinatus structural abnormalities of a subject's foot is provided. The device of the invention generally includes a compensatory wedge of a polyethylene foam material exhibiting a hardness in the range of 30 to 35 durometer. The wedge may be located between the subject's foot and footwear at the location of the recessed abnormality. In a preferred embodiment, the wedge is wedge-shaped laterally of the foot so as to compensate for a varus or valgus recessed structural foot abnormality. The polyethylene foam material preferably has a micro-structure comprised of fine, open cells, so as to allow for sufficient air flow and heat dissipation when in use to thereby reduce discomfort.

12 Claims, 2 Drawing Sheets

U.S. PATENT DOCUMENTS

| | | | |
|---|---|---|---|
| 4,979,318 A | 12/1990 | Cohen | |
| 4,982,737 A | 1/1991 | Guttmann | |
| 5,036,851 A | 8/1991 | Cohen | |
| 5,069,212 A | 12/1991 | Cohen | |
| 5,097,607 A | 3/1992 | Fredericksen | |
| 5,129,395 A | 7/1992 | Hoffmann | |
| 5,170,572 A | 12/1992 | Kantro | |
| 5,212,894 A | 5/1993 | Paparo | |
| D335,951 S | 6/1993 | Frachey et al. | |
| D340,349 S | 10/1993 | Kilgore et al. | |
| D341,022 S | 11/1993 | Zona | |
| 5,282,328 A | 2/1994 | Peterson | |
| 5,327,663 A | 7/1994 | Pryce | |
| 5,345,701 A | 9/1994 | Smith | |
| D354,616 S | 1/1995 | Schroer, Jr. | |
| D380,290 S | 7/1997 | Nakagawa | |
| D396,550 S | 8/1998 | Feldman et al. | |
| D397,238 S | 8/1998 | Lozano et al. | |
| 6,041,523 A | 3/2000 | Deloreia | |
| 6,092,314 A | 7/2000 | Rothbart | |
| 6,098,319 A | 8/2000 | Epstein | |
| 6,105,283 A | 8/2000 | Park | |
| 6,120,473 A | 9/2000 | Oliverio | |
| 6,141,890 A | 11/2000 | Chtn | |
| 6,170,176 B1 | 1/2001 | Clough | |
| 6,238,359 B1 | 5/2001 | Anderson | |
| 6,269,554 B1 | 8/2001 | Silvestrini et al. | |
| 6,270,872 B1 | 8/2001 | Cline et al. | |
| 6,277,088 B1 | 8/2001 | Novella | |
| 6,412,198 B1 | 7/2002 | Rothbart | |
| 6,460,273 B2 | 10/2002 | Witjes | |
| 6,477,793 B1 | 11/2002 | Pruitt et al. | |
| 6,585,674 B2 | 7/2003 | Toda | |
| 6,604,301 B1 | 8/2003 | Manoli, II et al. | |
| D483,556 S | 12/2003 | Zehr | |
| D484,299 S | 12/2003 | Van Diepen et al. | |
| 6,694,648 B2 | 2/2004 | Eriksen | |
| 6,725,578 B2 | 4/2004 | Kerrigan | |
| D496,526 S | 9/2004 | Grisoni et al. | |
| 2002/0005000 A1 | 1/2002 | Choi | |
| 2002/0056209 A1 | 5/2002 | Clough et al. | |
| 2002/0139011 A1 | 10/2002 | Kerrigan | |
| 2003/0005599 A1 | 1/2003 | Panaccione | |
| 2003/0005601 A1 | 1/2003 | Kasahara | |
| 2003/0041481 A1 | 3/2003 | Evans et al. | |
| 2004/0010945 A1 | 1/2004 | Erikson | |
| 2004/0025377 A1 | 2/2004 | Brannon | |
| 2004/0194344 A1 | 10/2004 | Tadin | |
| 2005/0039349 A1 | 2/2005 | Grisoni et al. | |

FOREIGN PATENT DOCUMENTS

| | | |
|---|---|---|
| WO | WO 99/04662 | 2/1999 |

* cited by examiner

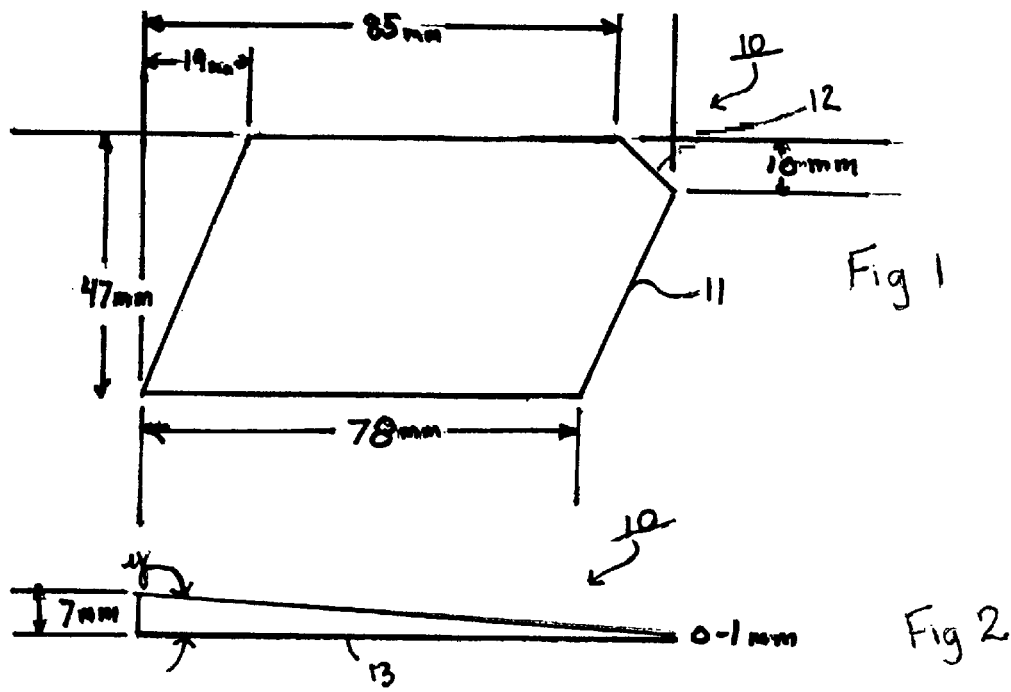
LEFT VALGUS WEDGE
(mirror image for right)
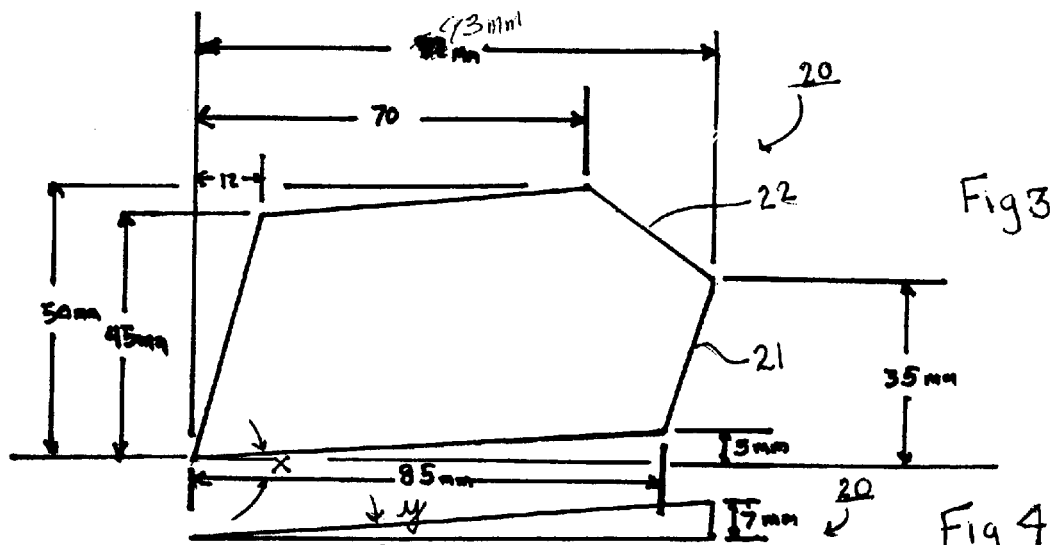
LEFT VARUS WEDGE
(mirror image for right)

ORTHOPEDIC FOOT DEVICES

FIELD OF INVENTION

The present invention relates generally to orthopedic compensatory devices applied to or under the foot. More particularly, the invention relates to podiatric devices for the restoration of normal or near normal function in the treatment of structural foot abnormalities.

BACKGROUND OF THE INVENTION

Orthopedic devices for the feet are well known, and have been used by laypersons and podiatrists for many years. Devices of this type range from a simple arch support to a custom formed orthotic to hold and control the foot. It has been estimated that 50% of the population could benefit from some form of device to improve function, stability, and balance for the super-imposed musculoskeletal system.

Foot misalignment can result in many forms of discomfort for the patient. Symptoms known to develop from such misalignment are plantar fasciitis, hammertoes, bunions, achilles tendonitis, and others. Misalignment can also cause or exacerbate knee, hip or back pain.

More particularly, structural malalignment of the foot is generally localized to either the fore foot, the rear foot, or combinations of both. These structural abnormalities may be generically classified as either of the varus or valgus type. The valgus abnormality refers specifically to a foot position, or any part thereof, wherein the joint is turned outward or everted, that is away from the body midline to an abnormal degree. The varus abnormality, on the other hand, is a condition of the foot, or any part thereof, being turned inward or inverted, that is towards the body midline to an abnormal degree.

Previous applications of prior art devices to a shoe, or insole in a shoe, that have been designed to correct structural abnormalities are known. See, for example, U.S. Pat. Nos. 4,333,472 and 5,345,701. However, the prior art devices have various drawbacks. As such, improvements of these devices are still needed.

SUMMARY OF THE INVENTION

An object of the present invention is to provide a podiatric orthopedic device that is to be applied to the human foot.

Another object of the present invention is to provide an orthopedic device that is to be disposed in footwear and worn for the correction and/or compensation of specifically identified structural biomechanical abnormalities of the human foot.

A further object of the present invention is to provide a series of uniquely configured orthopedic devices that are to be applied inside footwear in relation to a specific anatomical area exhibiting a structural biomechanical abnormality, thereby reducing or eliminating the manifest symptoms resulting from said specific structural foot abnormality.

Another object of the present invention is to provide a series of uniquely configured prosthetic orthopedic wedge-shaped devices that are to be applied inside footwear in either the anatomically defined rear foot or fore foot regions.

Another object of the present invention is to provide a series of uniquely configured orthopedic wedge-shaped devices to be applied inside footwear for the specific compensation of that structural biomechanical abnormality of the foot classified as either varus, valgus or a supinatus in nature.

A series of differentially-sized irregularly-shaped specifically configured generally wedge-shaped orthopedic prosthetic compensatory-corrective devices being of polyethylene foam material or like composition, are utilized in the treatment of specific clinical structural biomechanical abnormalities of the human foot. These unique prosthetic compensatory-corrective orthopedic foot wedges are disposed in relation to specifically identified anatomical regions in the footwear of the subject. Both the rear foot and the fore foot of the identified specific structural corrective regions, with either or both a varus or valgus correction being the indicated choice of application.

Other objects and advantages of the present invention will be apparent from the following description reference being had to the accompanying drawings wherein a preferred form of the embodiment of the present invention is clearly shown.

BRIEF DESCRIPTION OF THE DRAWINGS

FIG. 1 is a top view of a preferred valgus fore foot wedge of the present invention;

FIG. 3 is a top view of a preferred varus fore foot wedge of the present invention;

FIG. 4 is a side view of a preferred varus fore foot wedge of the present invention;

DESCRIPTION OF THE PREFERRED EMBODIMENT

Figure 2A:
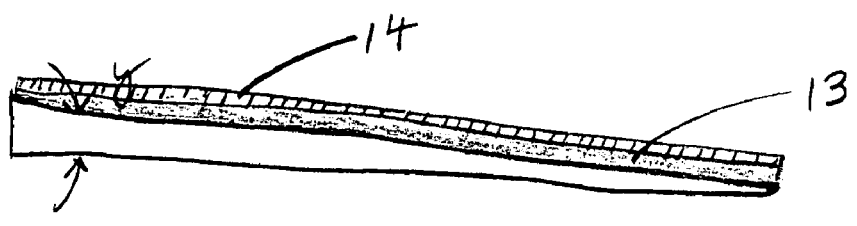
FIG. 2 is a side view of a preferred valgus fore foot wedge of the present invention

Referring now to the drawings and more particularly to FIGS. 1 and 2, which are top and side views of a preferred left valgus fore foot wedge of the present invention respectively, the valgus fore foot wedge 10 generally forms a substantially parallelogram outline, wedge-shaped configuration (a right valgus fore foot cushion pad being a mirror configuration). The top portion 12 of the interior edge 11 of the parallelogram, with reference to the fore foot, may be tapered such that the interior edge 11 extends to a point at a location corresponding to the first or second metatarsal phalangeal joint so as to better accommodate the structure of the fore foot. The angle γ is preferably in the range of from 2 degrees to 6 degrees, depending on the extent of correction desired. More specifically, the valgus wedge of the invention is preferably adapted to as to be placed with its thickest portion directly under the fifth metatarsal phalangeal joint, extending medially and tapering to an end point between the first and second metatarsal phalangeal joint. The thickest portion of the valgus wedge is preferably under the fifth metatarsal phalangeal joint with a gradual complete tapering to the first or second metatarsal phalangeal joint. The lower surface, upper surface, or both of the valgus wedge, as well as the other devices of the present invention, may be supplied with an adhesive coating for securing to the foot or footwear. The adhesive coating may optionally be covered by a peel-off protective covering.

FIGS. 3 and 4 are top and side views of a preferred varus fore foot cushion pad of the present invention, respectively (a right varus fore foot cushion pad being a mirror configuration). The varus fore foot cushion pad 20 is also generally of a substantially parallelogram, wedge-shaped configuration. The top portion 22 of the interior edge 21 of the parallelogram, with reference to the fore foot, may be tapered such that the interior edge 21 extends to a point at a location corresponding to the fourth metatarsal interspace (i.e., between the fourth and fifth metatarsal phalangeal joints) so as to better accommodate the structure of the fore foot. Again, the angle y of the wedge in this structural configuration may vary in the range of between 2 degrees and 6 degrees, while the outline of the pad is oblique at an angle x that is on the order of 30 degrees. The lower surface, upper surface, or both of the varus cushion pad may be supplied with an adhesive coating for securing to the foot or footwear. The adhesive coating may optionally be covered by a peel-off protective covering.

As such, in a preferred embodiment, the wedge of the invention may be of a substantial parallelogram, wedge-shaped configuration. However, other irregular, wedge-shaped configurations may be utilized, so long as the desired compensation/correction of the structural abnormality is achieved. For instance, the wedge may outlined shape such as a trancated solid pyramid. In any event, the overall length of a fore foot cushion pad of the invention mas vary as desired, preferably ranging in length between 2.5 to 3.5 inches. The overall width of a fore foot wedge may vary as desired, preferably in the range of 1.5 to 2.0 inches. The thickness of the cushion pad at its highest point being oppisite the wedge angle may vary as desired to achieve the desired wedge angle, preferably from about 5 to 9 mm, while its lowest point, at the angle position, varying from shout 0.1 mm to 1 mm. However, it is understood that the foregoing dimensions of the embodiment of the present invention are provided merely by way of explanation and are not intended to limit the invention in any fashion.

The fore foot valgus cushion pad is preferably positioned with the highest point of the wedge situated under the distal portion of the fifth metatarsal bone, and the fifth proximal phalanx. The wedge preferably extends transversely beneath the fourth, third, and second metatarsal bones as well as the fourth, third, and second proximal phalanges. This placement of the fore foot valgus cushion pad is specific for valgus structural abnormalities located in the fore foot region. The fore foot varus cushion pad is preferably positioned with the highest point of the wedge situated under the distal portion of the first metatarsal bone, and the first proximal phalanx. The fore foot varus cushion pad preferably extends transversely beneath the second, third, fourth, and fifth metatarsal bones, as well as the second, third, fourth, and fifth proximal phalanges. This placement of the fore foot varus cushion pad being specifically designed for compensation of varus structural abnormalities of the fore foot region.

The orthopedic devices of the invention may be constructed of a polyethylene foam material that simulates the hardness, flexibility, and rebound of a healthy foot fat pad. In this regard, the polyethylene foam material should preferably exhibit a hardness sufficient to accommodate the specific structural abnormality to be addressed. In one embodiment, the polyethylene foam material exhibits a hardness of about 20 to 40 durometer hardness units, more preferably 30 to 35 durometer hardness units, and even more preferably about 30 durometer hardness units. In a preferred embodiment, the polyethylene foam material has a microstructure comprised of fine, open cells, so as to allow for sufficient air flow and heat dissipation when in use. The polyethylene foam material may additionally be perforated to increase air flow and heat dissipation. A particularly preferred polyethylene foam material is UCOlite®, manufactured by UCO International. However, any other materials known in the art with similar hardness and cell structure may be used to form the orthopedics of the invention.

As mentioned above, the wedges of the present invention may be provided with an adhesive layer to position and secure the pad under the foot at the desired location. Any suitable adhesive known in the art may be employed. However, it should be noted that if the wedge is intended to be applied directly to the foot, a non-irritating adhesive should be used. In one embodiment, the adhesive layer may be applied to the upper surface of the pad, such that the pad may be secured directly to the foot of a wearer or to the underside of the sock liner of footwear at the desired location. Alternatively, the adhesive layer may be applied to the lower surface of the pad, such that the pad may be secured to the upper-side of the sock liner of footwear, or to the insole of footwear at the desired location.

In an alternative embodiment, the wedge of the invention may be directly integrated into an insole at the desired location. Thus, in one embodiment, the orthopedic device of the invention may comprise an insole with a wedge of the invention integrated along its length at a desired location.

In another aspect of the invention, an insole is provided with markings to indicate a desired placement of a wedge of the invention. As such, in one embodiment, the invention is directed to a orthopedic device kit comprising an insole with markings on the upper and/or lower surface to indicated a desired placement for a cushioning device of the invention, and instructions for placement of the cushioning device. The markings may preferably be ink lines to outline the desired placement of the wedge.

An individual's specific foot structural abnormality might require more than one device being applied to one foot at the same time. An example of this might be the need for the clinical application of both a fore foot valgus corrective pad, as well as a calcaneous rear foot cushion pad in the subject's footwear. Further, it has been noted clinically, that in numerous cases a need for the application of the present devices to both of the subject's feet has been necessary in order to successfully resolve the clinical symptoms arising from the structural abnormalities of the feet. A distinguishing feature of the present invention is the further availability of a multiple series of progressively graded sizes of the orthopedic devices, allowing a specific choice for a structural abnormality correction to be properly made.

Clinical studies have further indicated that prolonged and proper specific application of the devices of the present invention, have led consistently to marked clinical improvement in the symptoms arising from a subject's specific structural foot abnormality without the drawback of the prior art devices.

While the invention has been described in connection with a preferred embodiment, it is understood that the invention is not so limited. As recognized by one of skill in the art, numerous alternatives, modifications, and equivalents may be included within the spirit and scope of the invention as defined by the appended claims.

What is claimed:

1. An orthopedic device to compensate for varus or valgus structural abnormalities of a subject's foot, the device comprising a compensatory wedge of a foam material exhibiting a hardness sufficient to accommodate the correction of the subject's structural abnormality, wherein the wedge is placed under the subject's fore foot and under the location of the structural abnormality, wherein the wedge is shaped laterally and/or medially of the foot so as to compensate for either a varus or valgus structural fore foot abnormality, wherein the wedge comprises an outer perimeter which is substantially parallelogram in shape and wherein the wedge is shaped so as to taper from a thickest portion at one edge to a thinnest portion at the opposite edge, wherein the wedge further includes a clipped corner that extends to a point at a location corresponding to a metatarsal phalangeal joint or metatarsal interspace so as to accommodate anatomical structure and/or function of the fore foot, and wherein the foam material of the wedge has a microstructure comprised of open cells, so as to allow for sufficient air flow and heat dissipation when in use to thereby reduce discomfort.

2. An orthopedic device of claim 1 wherein the foam material exhibits a hardness in the range of 30 to 35 durometer.

3. An orthopedic device of claim 1 wherein the foam material is perforated to increase air flow and heat dissipation.

4. An orthopedic device of claim 1 further comprising an insole layer adapted for positioning within footwear, wherein the wedge is integrated along the width of the insole layer at the location of the structural abnormality under the fore foot.

5. An orthopedic device of claim 1 wherein the wedge, with reference to the fore foot, is adapted so as to be placed with its thickest portion directly under the fifth metatarsal phalangeal joint, extending medially and tapering to an end point between the first and second metatarsal phalangeal joint, to thereby accommodate for the abnormal structural valgus deformity of the fore foot.

6. An orthopedic device of claim 1 wherein the wedge is adapted for fore foot abnormalities and configured so as to be disposed in the subject's footwear in the region of the distal metatarsal bones.

7. An orthopedic device of claim 1 wherein the lower surface, the upper surface, or both of the wedge is coated with an adhesive substance for securing the device in a subject's footwear or directly to a subject's foot.

8. The orthopedic device of claim 7 wherein the adhesive substance of the device is further covered with a protective layer prior to its application.

9. An orthopedic device of claim 1 wherein the foam material is a polyethylene foam material.

10. An orthopedic device of claim 1 wherein the corner of the wedge just distal to the second metatarsal head is clipped and cut on a bias oriented medially and proximally of the fore foot so as to accommodate for the abnormal structural valgus deformity of the fore foot.

11. An orthopedic device of claim 1 wherein the wedge, with reference to the fore foot, is adapted to as to be placed with its thickest portion directly under the first metatarsal phalangeal joint, extending medially and tapering to an end point between the fourth and fifth metatarsal phalangeal joint, and having the corner most distal to the first metatarsal head clipped and cut on a bias oriented medially and proximally of the fore foot to thereby accommodate for the abnormal structural varus deformity of the fore foot.

12. An orthopedic device of claim 1 wherein the clipped corner extends to a point at a location corresponding to the fourth metatarsal interspace so as to accommodate for the abnormal structural varus deformity of the fore foot.

* * * * *